US00PP11953P2

(12) United States Plant Patent
Ruigrok

(10) Patent No.: US PP11,953 P2
(45) Date of Patent: Jun. 26, 2001

(54) DAHLIA PLANT NAMED 'LISA PEARL'

(76) Inventor: Frank N. G. Ruigrok, Hyacintenlaan 15, 2182 DE Hillegom (NL)

( * ) Notice: Subject to any disclaimer, the term of this patent is extended or adjusted under 35 U.S.C. 154(b) by 0 days.

(21) Appl. No.: 09/233,135

(22) Filed: Jan. 19, 1999

(51) Int. Cl.[7] ..... A01H 5/00
(52) U.S. Cl. ..... Plt./321
(58) Field of Search ..... Plt./321

(56) References Cited

U.S. PATENT DOCUMENTS

| | | | | |
|---|---|---|---|---|
| P.P. 36 | * | 10/1932 | Broomall | Plt./321 |
| P.P. 1,386 | * | 4/1955 | Curtis et al. | Plt./321 |
| P.P. 6,767 | * | 5/1989 | Mulder | Plt./321 |
| P.P. 11,080 | * | 10/1999 | van Dongen | Plt./321 |
| P.P. 11,429 | * | 6/2000 | Verwer | Plt./321 |

OTHER PUBLICATIONS

GTITM UPOVROM Citation for 'Lisa' as per NL PBR DHL 0016; Jan. 18, 1993.*
GTITM UPOVROM Citation for 'Lisa' as per QZ PBR 952490; Feb. 22, 1996.*

Broertjes et al., Mutation Breeding of *Dahlia variabilis*, Euphytica, 16(2): 171–176, 1967.

Boyer et al., American Dahlia Society 1976–1989 List of Dahlias, pp. 1–2, 43 and 125, 1989.

Das et al., New Dahlias Through Irradiation, Indian Horticulture, 23(1): 19 and 21, 1978.

Gottschalk et al., Induced Matations in Plant Breeding, pp. 30–31 and 66–67, 1983.

* cited by examiner

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Dahlia plant named 'Lisa Pearl', characterized by its large and numerous double inflorescences that are about 7.9 cm in diameter; white ray florets; mostly upright, mounded and uniform growth habit; dark green leaves; and strong peduncles that hold inflorescences above the foliage.

1 Drawing Sheet

BACKGROUND OF THE INVENTION

The present invention relates to a new and distinct variety of Dahlia plant, botanically known as *Dahlia variabilis*, and hereinafter referred to by the cultivar name 'Lisa Pearl'.

The new Dahlia is a naturally-occurring whole plant mutation of the *Dahlia variabilis* cultivar 'Lisa', not patented. The new Dahlia was discovered by the Inventor in September, 1996 in a controlled environment in Hillegom, The Netherlands, within a population of plants of 'Lisa'. The selection of this plant was based on its unique ray floret color.

Asexual reproduction of the new Dahlia by terminal cuttings harvested in Hillegom, The Netherlands, has shown that the unique features of this new Dahlia are stable and reproduced true to type in successive generations.

BRIEF SUMMARY OF THE INVENTION

The new Dahlia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Lisa Pearl'. These characteristics in combination distinguish 'Lisa Pearl' as a new and distinct cultivar:

1. Large and numerous double inflorescences that are about 7.9 cm in diameter.

2. White ray florets.
3. Mostly upright, mounded and uniform growth habit.
4. Dark green leaves.
5. Strong peduncles that hold inflorescences above the foliage.

Compared to plants of the parent cultivar, 'Lisa', plants of the new Dahlia have white ray florets whereas plants of the cultivar 'Lisa' have light pink ray florets. In addition, ray floret color of plants of the new Dahlia does not fade significantly with development, whereas ray floret color of plants of the cultivar 'Lisa' fades significantly with development.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which accurately describe the actual colors of the new Dahlia. The photograph comprises a top perspective view of a typical plant of the new Dahlia.

DETAILED BOTANICAL DESCRIPTION

In the following description, color references are made to The Royal Horticultural Society Colour Chart except where general terms of ordinary dictionary significance are used. The following observations and measurements describe plants grown in De Lier, The Netherlands, in 12-cm containers in a glass greenhouse with average day and night temperatures of 22 and 18° C, respectively. Plants were about 8 to 10 weeks old after planting.

Botanical classification: *Dahlia variabilis*. 'Lisa Pearl'.

Parentage: Naturally-occurring whole plant mutation of *Dahlia variabilis* cultivar 'Lisa', not patented.

Propagation:

*Type*.—By terminal cuttings.

*Time to initiate roots*.—Summer: About 5 days at 22° C. Winter: About 8 days at 20° C.

*Time to develop roots*.—Summer: About 12 days at 22° C. Winter: About 16 days at 20° C.

*Rooting habit and root description*.—Easily propagated; roots fine, fibrous and well-branched.

Plant description:

*Appearance*.—Typically grown as potted flowering plants. Mostly upright, mounded and uniform growth habit; rounded plant apex. Moderate growth rate and moderately vigorous. Appropriate for 10 to 12.5-cm containers. Plants typically flower about 8 weeks after planting rooted cuttings. Freely basally branching, however, plants typically require pinching to enhance lateral branch development.

*Plant height*.—About 27 cm.

*Plant spread*.—About 28 cm.

*Stem description*.—Lateral branch diameter: About 1.3 cm. Internode length: About 4.5 cm. Texture: Smooth. Color: 144A.

*Foliage description*.—Arrangement: Young foliage, leaves single; fully expanded foliage, leaves compound, trifoliate; opposite. Leaf length: About 14 cm. Leaf width: About 11 cm. Terminal leaflet length: About 9.5 cm. Terminal leaflet width: About 5 cm. Leaflet shape: Ovate. Leaflet apex: Acute. Leaflet base: Attenuate. Leaflet margin: Dentate. Leaflet texture: Glabrous. Petiole length: About 5.5 cm. Color: Young leaflets, upper surface: Greener than 147A. Young leaflets, lower surface: Lighter than 147B. Mature leaflets, upper surface: 147A. Mature leaflets, lower surface. Close to 147B. Petiole: 144A.

Flowering description:

*Appearance*.—Double inflorescence form. Inflorescences generally hemispherical and borne on terminals above foliage, arising from leaf axils on strong peduncles; inflorescences above the foliage. Inflorescences face upright and outward. Freely flowering, typically about 23 inflorescences per plant. Disc and ray florets arranged acropetally on a capitulum. Not fragrant.

*Flowering response*.—Under natural conditions, plants flower intermittently from late spring through fall.

*Inflorescence longevity*.—Inflorescences typically maintain good substance for about 1 to 2 weeks on the plant.

*Flower bud* (*just before opening*).—Shape: Flattened spherical. Length: About 1 cm. Diameter: About 1.2 cm. Color: 143A to 144A.

*Inflorescence size*.—Diameter: About 7.9 cm. Depth (height): About 2.2 cm. Disc floret diameter: About 1 cm; conspicuous only on fully opened inflorescences.

*Ray florets*.—Quantity per inflorescence: About 65. Shape: Broadly elliptic. Orientation: Initially upright to horizontal; cupped. Length: About 3.6 cm. Width: About 2 cm. Apex: Acute, emargimate, bifid or trifid. Base: Attenuate. Margin: Entire. Texture: Smooth, glabrous. Color: When opening, upper surface: Overall tonality, white 155D, with slight yellowish caste, close to 4D. When opening, lower surface: Overall tonality, white, 155D, with slight yellowish cast, close to 4D. Fully opened, upper surface: Overall tonality, white, 155D; base, yellowish white, close to 1B to 1C; under cool production temperatures apices may show a faint light pink tone, close to 65B to 65D; iridescent. Fully opened, lower surface: Overall tonality, white, 155D; base, yellowish white, close to 1C; under cool production temperatures apices may show a faint light pink tone, close to 65C to 65D; iridescent.

*Disc florets*.—Quantity per inflorescence: About 21. Shape: Tubular. Orientation: Upright. Length: About 1.2 cm. Width: Apex: About 3 mm. Base: About 1 mm. Apex: Pentafid. Color: Apex: 9A. Mid-section: 17A. Base: Light green.

*Peduncle*.—Aspect: Upright and strong. Length: About 13.25 cm. Diameter: About 4 mm. Texture: Smooth. Color: 144A.

*Involucral bracts*.—Shape: Oblong to linear. Tip: Acute to rounded. Margin: Entire. Texture: Waxy. Color: 144A to 144C.

*Reproductive organs*.—Androecium: Present on disc florets only. Anther color 9A. Pollen amount: Moderate. Pollen color: 17A. Gynoecium: Present on disc and ray florets.

Disease resistance: Resistance to known Dahlia diseases has not been observed o plants grown under commercial greenhouse conditions.

Seed production: Seed production has not been observed.

It is claimed:

1. A new and distinct cultivar of Dahlia plant named 'Lisa Pearl', as illustrated and described.

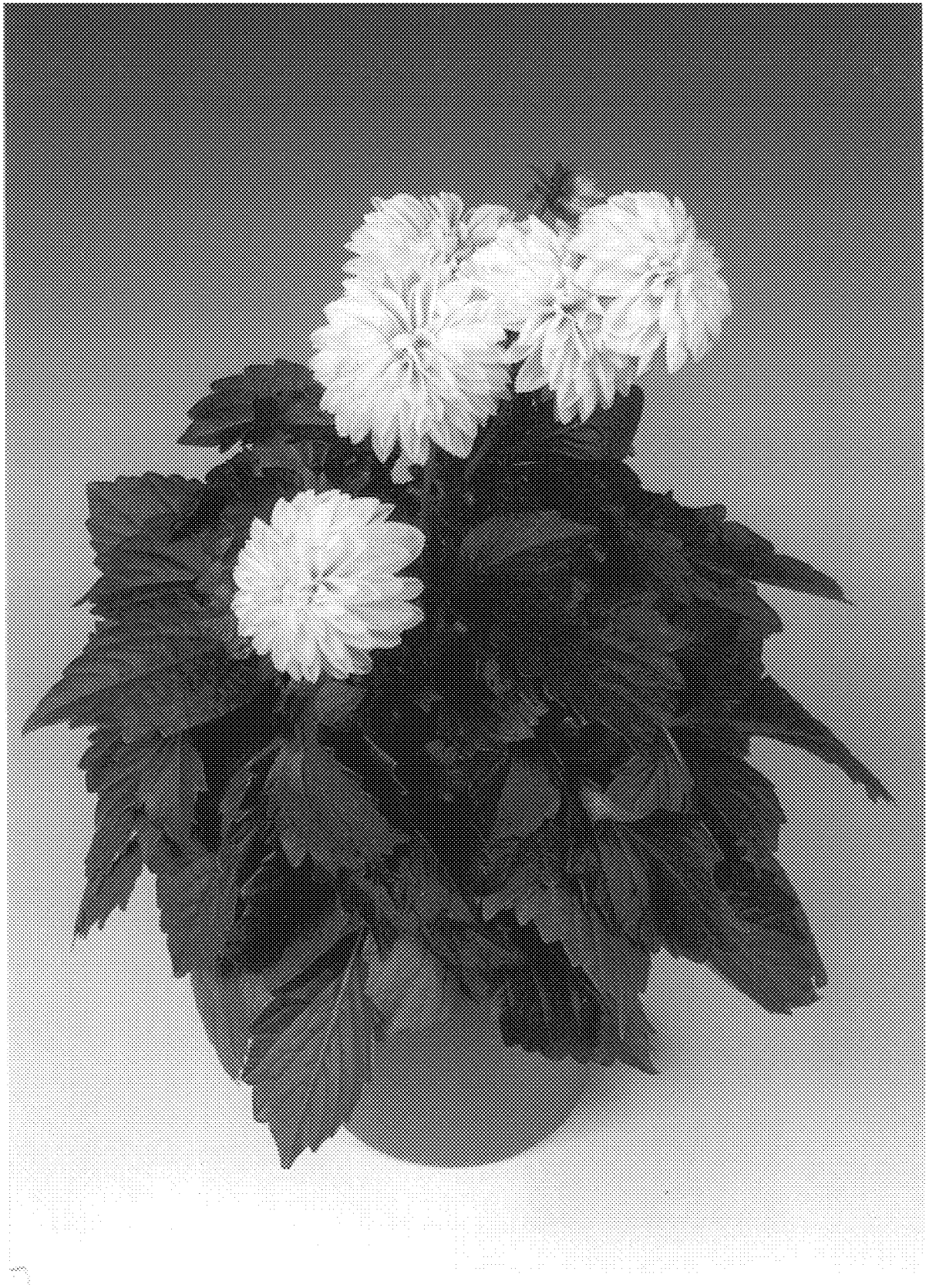

* * * * *